(12) United States Patent  
Okiyama

(10) Patent No.: US 8,276,875 B2  
(45) Date of Patent: Oct. 2, 2012

(54) PLATE CLAMP

(75) Inventor: Tadashi Okiyama, Hiroshima (JP)

(73) Assignee: JMS Co., Ltd., Hiroshimashi (JP)

( * ) Notice: Subject to any disclaimer, the term of this patent is extended or adjusted under 35 U.S.C. 154(b) by 624 days.

(21) Appl. No.: 12/296,809

(22) PCT Filed: Apr. 14, 2006

(86) PCT No.: PCT/JP2006/307911  
§ 371 (c)(1),  
(2), (4) Date: Jan. 16, 2009

(87) PCT Pub. No.: WO2007/122681  
PCT Pub. Date: Nov. 1, 2007

(65) Prior Publication Data  
US 2009/0189099 A1  Jul. 30, 2009

(51) Int. Cl.  
*F16K 7/04* (2006.01)

(52) U.S. Cl. ............. 251/4; 604/250; 606/142; 606/143

(58) Field of Classification Search .............. 251/4, 7, 251/8; 24/130, 570, 129 R, 561, 910, DIG. 8, 24/DIG. 9, 67 CF, 67.9, 67.3, 66.13, 3.12, 24/545, DIG. 29, DIG. 28; 604/250, 33, 604/249; D24/143, 129; D8/396; 248/72, 248/742; 606/142, 143  
See application file for complete search history.

(56) References Cited

U.S. PATENT DOCUMENTS

| | | | | |
|---|---|---|---|---|
| 3,314,371 A * | 4/1967 | Hopkinson | .................... | 417/479 |
| 3,357,674 A * | 12/1967 | Coanda et al. | ..................... | 251/7 |
| D233,312 S * | 10/1974 | Lock | ............................. | D24/143 |
| 4,248,401 A * | 2/1981 | Mittleman | ........................ | 251/7 |
| 4,307,869 A * | 12/1981 | Mittleman | ........................ | 251/7 |
| 4,432,121 A * | 2/1984 | Dupre | ............................. | 24/343 |
| 4,434,963 A * | 3/1984 | Russell | ............................... | 251/7 |
| D279,314 S * | 6/1985 | Ishida et al. | ................. | D24/143 |
| 4,619,020 A * | 10/1986 | Lecher, Sr. | .................... | 24/10 A |
| 4,690,162 A * | 9/1987 | Lyddy et al. | ....................... | 137/1 |
| 4,932,629 A * | 6/1990 | Rodomista et al. | ............... | 251/4 |
| D316,038 S * | 4/1991 | Gagnet | .......................... | D9/435 |
| 5,401,256 A * | 3/1995 | Stone et al. | .................... | 604/250 |
| 5,593,392 A * | 1/1997 | Starchevich | .................. | 604/246 |
| 6,840,492 B1 * | 1/2005 | Boyne-Aitken | .................. | 251/7 |
| 7,124,996 B2 * | 10/2006 | Clarke et al. | ....................... | 251/7 |
| 2008/0319402 A1 * | 12/2008 | Howlett et al. | ............... | 604/250 |

FOREIGN PATENT DOCUMENTS

| | | |
|---|---|---|
| JP | 8-57048 A | 3/1996 |
| JP | 2003-185061 A | 7/2003 |

OTHER PUBLICATIONS

International Search Report of PCT/JP2006/307911, date of mailing May 23, 2006.

\* cited by examiner

*Primary Examiner* — John K Fristoe, Jr.  
*Assistant Examiner* — Marina Tietjen  
(74) *Attorney, Agent, or Firm* — Westerman, Hattori, Daniels & Adrian, LLP

(57) ABSTRACT

A plate clamp where clamp resistance when a tube is slid from an insertion hole to a slit section is low, where clamping operation is easy, and where the tube being clamped at the slit section is less likely to unintentionally slide to the through-hole side. The clamp for a tube has the slit section for clamping and holding the tube at plate-like members, a tube lead-in section as a groove forwardly expanding from the forward end of the slit section, and the tube insertion hole continuously formed with the tube lead-in section. A stopper section is provided only on one side of the boundary between the tube lead-in section and the slit section.

3 Claims, 2 Drawing Sheets

[Fig.1] PRIOR ART
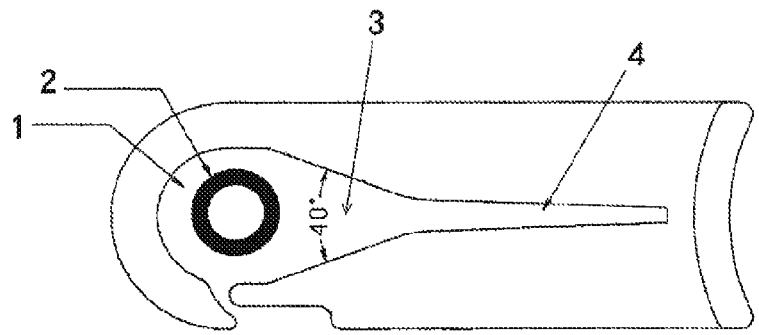
[Fig.2] PRIOR ART
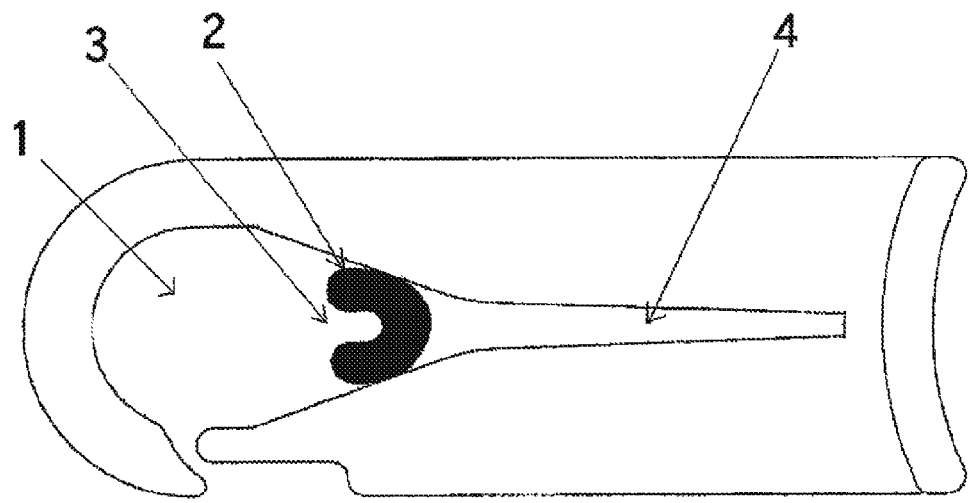
[Fig.3]
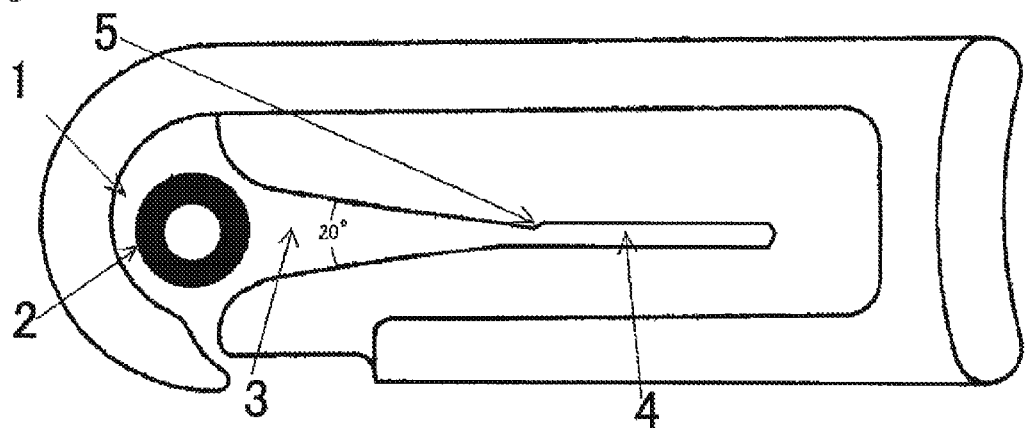

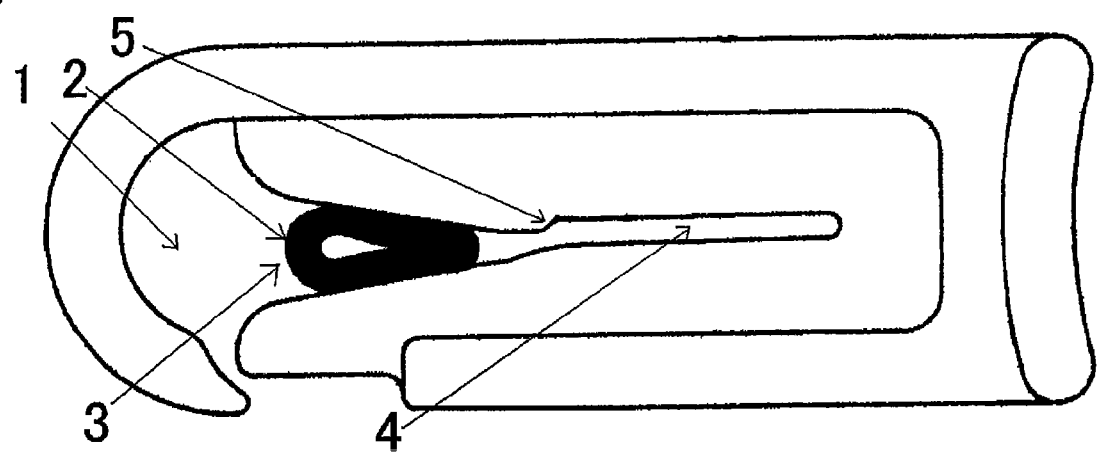

PLATE CLAMP

TECHNICAL FIELD

The present invention relates to a plate clamp used to pinchingly hold a tube.

BACKGROUND ART

As shown in FIG. 1, a conventional plate clamp is composed of a tube insertion hole 1 through which a tube 2 is inserted, a slit section 4 in which the tube 2 is clamped, and a tube lead-in section 3. The tube 2 located in the tube insertion hole 1 is slid to the slit section 4 to clamp the tube 2. However, depending on a tube material or size, the tube 2 may be deformed into a U shape as shown in FIG. 2, thus increasing slide resistance to make the sliding difficult. Furthermore, repeated sliding may cause the tube 2 to be worn away to reduce the strength of the tube 2. Coating of an inner surface of the clamp with a lubricant has been proposed to solve the above-described problems (Patent Document 2). However, although the lubricant coating the clamp is effective for reducing the slide resistance during clamping, the sliding resistance in the area from the slit section to the insertion hole also decreases to increase the risk of an accident in which the clamp slips unintentionally out of the slit section.

Patent Document 1: Japanese Utility Model Laid-Open No. 63-1541

Patent Document 2: Japanese Patent No. 3517284

DISCLOSURE OF THE INVENTION

An object of the present invention is to provide a plate clamp which has a low clamp resistance to, for example, a tube sliding from an insertion hole to a slit section, thus enabling an easy clamp operation and which also serves to reduce the risk of slipping the tube pinchingly fitted in the slit section of a clamp out of the slit section even if the interior of the clamp is treated with a lubricant.

The present invention has accomplished the object by providing a tube clamp comprising a slit section allowing a plate-like member to pinchingly hold a tube, a tube lead-in section that is a groove expanding forward from a forward end of the slit section, and a tube insertion hole that is continuous with the tube lead-in section, the clamp being characterized in that a stopper section of the tube is provided only on one side of a boundary between the tube lead-in section and the slit section.

In the clamp according to the present invention, a lubricant layer is formed on an inner surface of the clamp in order to reduce the clamp resistance to the tube sliding from the tube insertion hole to the slit section, thus enabling an easy clamp operation. This enables avoidance of the risk of slipping the tube pinchingly fitted in the slit section of the clamp out of the slit section.

Furthermore, in the clamp according to the present invention, if the angle of a lead-in section of the tube increases, for example, if the angle exceeds 30 degrees, the sliding may be difficult because when the tube slides from the insertion hole toward the slit section, the tube may be deformed into a "V" shape at the lead-in section adjacent to an entrance side of the slit section for the tube as shown in FIG. 2. However, when the angle of the lead-in section for the tube is reduced to, for example, 20±10 degrees, preferably 20±5 degrees, more preferably about 20 degrees, the tube can be deformed into a straight line shape instead of the "V" shape. The slide resistance to the tube sliding from the insertion hole to the slit section is thus reduced. This is very effective means for solving the above-described problems. However, the adoption of an angle of less than 30 degrees as described above, for example, an angle of 20±5 degrees, also involves a high risk of slipping the tube pinchingly fitted in the slit section out of the slit section as is the case with the use of the lubricant. However, formation of the stopper section enables avoidance of the risk.

BRIEF DESCRIPTION OF THE DRAWINGS

FIG. 1 is a diagram illustrating the configuration of a conventional plate clamp including a tube lead-in section with an angle of 40 degrees and no slide resistance section;

FIG. 2 is a diagram of the plate clamp in FIG. 1, illustrating that a tube has been deformed into a "V" shape;

FIG. 3 is a diagram illustrating the configuration of a plate clamp according to the present invention including a tube lead-in section with an angle of 20 degrees and a slide resistance section; and FIG. 4 is a diagram of the plate clamp in FIG. 3, illustrating that a tube has been deformed into a straight line shape.

DESCRIPTION OF SYMBOLS

1 Tube insertion hole, 2 Tube, 3 Tube lead-in section, 4 Slit section, 5 Stopper section

BEST MODE FOR CARRYING OUT THE INVENTION

The configuration and function of a plate clamp according to the present invention will be specifically described with reference to FIGS. 3 and 4.

Embodiment 1

Components of a plate clamp according to the present embodiment are all produced by integrally molding a polypropylene polyacetal resin. The clamp has a slit section 4 allowing a plate-like member to pinchingly hold a tube 2, a tube lead-in section 3 that is a groove expanding forward from a forward end of the slit section 4, a tube insertion hole 1 that is continuous with the tube lead-in section 3, and a stopper section 5 for the tube formed only on one side of a boundary between the tube lead-in section 3 and the slit section 4. The tube insertion hole 1 is formed to be partly open. However, the tube insertion hole in the plate clamp according to the present invention may avoid having an open section.

Preferably, the tube lead-in section 3 has a function of allowing the tube to slide from the through-hole 1 to the slit section 4, and is formed to have a small angle such that the tube 2 can be deformed into a straight line shape at the boundary of the slit section 4. Although the value of the small angle depends on the thickness or diameter of the tube or the characteristics of a material forming the tube, an angle of greater than 30 degrees makes deforming the tube 2 into the straight line shape difficult, whereas an angle of smaller than 10 degrees requires a significant increase in the length of the tube lead-in section 3 in order to fulfill the function of the tube lead-in section 3, resulting in an increase in the size of the clamp. Thus, the angle is preferably at least 10 degrees and less than 30 degrees, and more preferably 20±5 degrees, and particularly preferable angles are about 20 degrees and those close to 20 degrees. In contrast, in the plate clamp in FIGS. 1 and 2, illustrating the conventional technique, the tube lead-in section 3 has an angle of about 40 degrees, thus causing the tube 2 to be deformed into the "V" shape. This makes sliding of the tube from the tube lead-in section 3 to the slit section 4 difficult. In the present invention, including the present embodiment, the tube 2 deformed into the straight line shape refers to the flatly-deformed tube 2 leaving a part of the tube 2 open or without leaving the opening.

In the clamp according to the present embodiment, a stopper section 5 is formed only on one side of the boundary between the tube lead-in section 3 and the slit section 4 to offer a slide resistance force hindering the tube clamped in the slit section 4 from sliding into the through-hole. The stopper section 5 can be formed as an inclined step or a stage section at the boundary between the slit section 4 and the tube lead-in section 3 by, in the clamp corresponding to the one in which the stopper section 5 according to the present embodiment has not been formed yet, extending an inner surface of the tube lead-in section 3 on which the stopper section 5 is formed, further, toward the slit section 4 side, than an inner surface of the tube lead-in section 3 on which the stopper section 5 is not formed. The stopper section 5 configured as described above can be provided without the need to excessively reduce the slit section width, while maintaining an appropriate slit section width required to pinchingly hold the tube.

The clamp according to the present embodiment has advantages described below owing to the formation of the above-described stopper section 5. The appropriate ability of the tube to slide from the tube lead-in section 3 to the slit section 4 can be maintained with the predetermined slit section width maintained. Nevertheless, the ability of the stopper to prevent the tube from sliding in the opposite direction, from the slit section 4 to the tube lead-in section 3, can be improved to prevent the tube from being unexpectedly opened. In particular, in the clamp according to the present invention, the stopper section 5 needs to be provided only on one side of the boundary between the tube lead-in section 3 and the slit section 4 rather than on both sides of the boundary as described above. If the stopper section 5 as described above is provided on both sides of the boundary between the tube lead-in section 3 and the slit section 4, the above-described advantages are not provided.

Even in the clamp according to the present embodiment, the tube 2 can be easily slid from the through-hole 1 to the slit section 4 by treating at least a part of a surface of the tube lead-in section 3 and/or the slit section 4 with a lubricant or kneading the lubricant into a material forming the tube lead-in section 3 and the slit section 4. Furthermore, the lubricant treatment may disadvantageously reduce the slide resistance to the tube sliding from the slit section 4 to the tube insertion hole 1 as described above. However, the plate clamp according to the present invention allows this problem to be solved by the stopper section 5 formed as described above. Additionally, if a lubricative tube, for example, a tube with a surface treated with a lubricant or with a lubricant kneaded into the material thereof is clamped, it is unnecessary to improve the lubricative property of the clamp itself as described above. However, even in this case, the stopper section 5 can provide the stopper function of preventing the tube from sliding from the slit section 4 to the tube lead-in section 3.

Industrial Applicability

In the clamp according to the present invention, the stopper section 5 provided only on one side of the boundary between the tube lead-in section 3 and the slit section 4 can serve to maintain the appropriate ability of the tube to slide from the tube lead-in section 3 to the slit section 4 while maintaining the predetermined slit section width; the ability would be difficult to achieve if the stopper section 5 is provided on both sides of the boundary. Nevertheless, the clamp according to the present invention allows improvement of the ability of the stopper to prevent the tube from sliding in the opposite direction, from the slit section 4 to the tube lead-in section 3, to prevent the tube from being unexpectedly opened.

The invention claimed is:

1. A tube clamp comprising a plate-shaped member having a tube insertion hole;
    a slit section to allow the plate-like member to pinch and hold a tube;
    a tube lead-in section connecting the tube insertion hole and the slit section with a slope expanding from a forward end of the slit section toward the tube insertion hole with an angle of 10 to 30 degrees; and
    a stopper section having an inclined step or stage provided only on one side of a boundary between the tube lead-in section and the slit section, the stopper section being formed by extending an inner surface of the tube lead-in section on which the stopper section is formed, further toward the slit section side than an inner surface of the tube lead-in section on which the stopper section is not formed.

2. The tube clamp according to claim 1, wherein a lubricant layer is formed on at least a part of an inner surface of the tube lead-in section and/or the slit section.

3. The tube clamp according to claim 1 or 2, wherein the angle of the lead-in section is 25 to 15 degrees.

* * * * *